(12) United States Patent
Morgan et al.

(10) Patent No.: US 11,849,773 B2
(45) Date of Patent: Dec. 26, 2023

(54) KNIT ARTICLE WITH VARIABLE FEATURES

(71) Applicant: NIKE, Inc., Beaverton, OR (US)

(72) Inventors: Amir H. Morgan, Hillsboro, OR (US); Trina Z. Murrietta, Portland, OR (US); Daniel Shirley, Beaverton, OR (US); Liron Bilsky, Kfar Vradim (IL); David Malul, Beaverton, OR (US); Rotem Wilk Naftaly, Ein Dor (IL); Mohamed Omar, Der Al Asad (IL); Ronen Yehuda, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 0 days.

(21) Appl. No.: 17/525,623

(22) Filed: Nov. 12, 2021

(65) Prior Publication Data
US 2022/0205151 A1    Jun. 30, 2022

Related U.S. Application Data

(60) Provisional application No. 63/164,677, filed on Mar. 23, 2021, provisional application No. 63/157,890, (Continued)

(51) Int. Cl.
*D04B 1/02* (2006.01)
*A41B 11/02* (2006.01)
(Continued)

(52) U.S. Cl.
CPC ............ *A41B 11/02* (2013.01); *A41B 11/003* (2013.01); *A61F 2/7812* (2013.01); (Continued)

(58) Field of Classification Search
CPC ........ D04B 1/0043; D04B 1/102; D04B 1/18; D04B 1/265; D04B 1/04; D04B 1/26;
(Continued)

(56) References Cited

U.S. PATENT DOCUMENTS 1,806,492 A    5/1931    Nestler
2,050,535 A    8/1936    Martel
(Continued)

FOREIGN PATENT DOCUMENTS

DE    20219015 U1    4/2003
EP    2815728 B1    1/2016
(Continued)

OTHER PUBLICATIONS

A/K Brim Sheath, Knit-Rite, knitrite.com, Available online at: < http://www.knitrite.com/prosthetics/sheaths/brimsheath.html>, Nov. 2, 2012, 2 pages.

(Continued)

*Primary Examiner* — Danny Worrell
(74) *Attorney, Agent, or Firm* — SHOOK, HARDY & BACON L.L.P.

(57) ABSTRACT

Aspects herein are directed to a knit structure used to form a knit article where the knit structure can be adjusted to provide zoned cushioning, zoned insulation, zoned fit, zoned permeability/breathability features, and/or zoned tactile feedback features. The knit structure has a repeating pattern of a first number of knit courses having a first yarn knit with a first basic knit stitch and a second number of knit courses, where within each knit course of the second number of knit courses, the first yarn is knit in a repeating pattern having a first number of knit stitches knit with a second basic knit stitch and a second number of float stitches knit with a float stitch to form float areas.

20 Claims, 9 Drawing Sheets

Related U.S. Application Data filed on Mar. 8, 2021, provisional application No. 63/132,593, filed on Dec. 31, 2020.

(51) Int. Cl.

| | | |
|---|---|---|
| *A41B 11/00* | (2006.01) | |
| *D03D 1/00* | (2006.01) | |
| *A61F 2/78* | (2006.01) | |
| *D04B 1/26* | (2006.01) | |
| *D04B 1/10* | (2006.01) | |
| *D04B 1/18* | (2006.01) | |

(52) U.S. Cl.
CPC .......... *D03D 1/0043* (2021.05); *D04B 1/102* (2013.01); *D04B 1/18* (2013.01); *D04B 1/265* (2013.01); *A61F 2002/7837* (2013.01); *D10B 2401/041* (2013.01); *D10B 2509/00* (2013.01)

(58) Field of Classification Search
CPC .......... D04B 1/243; D04B 1/246; D04B 1/02; D04B 1/025; D04B 7/12; D04B 9/12; A41B 11/02; A41B 11/003
See application file for complete search history.

(56) References Cited

U.S. PATENT DOCUMENTS

| | | |
|---|---|---|
| 2,102,368 A | 12/1937 | Martel |
| 2,279,919 A | 4/1942 | Harry |
| 2,926,512 A | 3/1960 | Robertson |
| 3,130,566 A | 4/1964 | Chesebro |
| 3,601,818 A | 8/1971 | Chesebro et al. |
| 3,793,851 A | 2/1974 | Thorneburg |
| 3,975,929 A | 8/1976 | Fregeolle |
| 3,991,424 A | 11/1976 | Prahl |
| 4,034,580 A | 7/1977 | Holder |
| 4,034,581 A | 7/1977 | Swafford |
| 4,038,699 A | 8/1977 | Burn |
| 4,149,274 A | 4/1979 | Garrou et al. |
| 4,237,707 A | 12/1980 | Coble et al. |
| 4,282,727 A | 8/1981 | Dunlap et al. |
| 4,282,728 A | 8/1981 | Tapp et al. |
| 4,326,393 A | 4/1982 | Dunlap |
| 4,341,096 A | 7/1982 | Safrit et al. |
| 4,494,388 A | 1/1985 | Lau et al. |
| 4,514,863 A | 5/1985 | Tuyet-van |
| 4,520,635 A | 6/1985 | Shields et al. |
| 4,522,044 A | 6/1985 | Lineberry et al. |
| 4,702,091 A | 10/1987 | Good et al. |
| 4,732,015 A | 3/1988 | Abrams et al. |
| 5,307,522 A | 5/1994 | Throneburg et al. |
| 5,335,517 A | 8/1994 | Throneburg et al. |
| 5,412,957 A | 5/1995 | Bradberry et al. |
| 5,428,975 A | 7/1995 | Lee et al. |
| 5,603,232 A | 2/1997 | Throneburg |
| 5,708,985 A | 1/1998 | Ogden |
| 5,809,575 A | 9/1998 | Chen |
| 5,931,872 A | 8/1999 | Lohmann |
| 6,079,235 A | 6/2000 | Schmidt |
| 6,149,690 A | 11/2000 | Belzidsky |
| 6,324,874 B2 | 12/2001 | Fujimoto |
| 6,708,342 B2 | 3/2004 | Boersema |
| 6,871,516 B2 | 3/2005 | Peeler et al. |
| D503,802 S | 4/2005 | Bjarnason |
| 6,964,688 B1 | 11/2005 | Kania |
| 7,076,973 B1 | 7/2006 | Chesebro et al. |
| 7,169,189 B2 | 1/2007 | Bjarnason et al. |
| D590,590 S | 4/2009 | Bonzagni et al. |
| 7,677,061 B2 | 3/2010 | Mori et al. |
| 7,699,195 B2 | 4/2010 | Scott |
| 7,748,240 B1 | 7/2010 | Cherneski |
| D634,925 S | 3/2011 | Gesser et al. |
| D643,207 S | 8/2011 | Hollingsworth et al. |
| 8,051,498 B2 | 11/2011 | Ganzoni et al. |
| 8,220,077 B1 | 7/2012 | Ott et al. |
| 8,544,300 B2 | 10/2013 | Kaneda et al. |
| D740,014 S | 10/2015 | Amis |
| D747,601 S | 1/2016 | Middleton |
| 9,301,552 B2 | 4/2016 | Dickson |
| 9,358,172 B2 | 6/2016 | Collins et al. |
| D762,057 S | 7/2016 | Hakeem |
| D773,798 S | 12/2016 | Amis |
| D776,913 S | 1/2017 | Hakeem |
| 9,603,748 B2 | 3/2017 | Valois et al. |
| 10,011,926 B2 | 7/2018 | Gaither |
| 10,271,968 B2 | 4/2019 | Bache et al. |
| 10,376,391 B2 | 8/2019 | Halldorsson et al. |
| 10,501,874 B2 | 12/2019 | Kostian |
| D895,264 S | 9/2020 | Manning et al. |
| 11,401,636 B2 | 8/2022 | Amis et al. |
| 2005/0149202 A1 | 7/2005 | Schaffer et al. |
| 2007/0162153 A1 | 7/2007 | Barnes et al. |
| 2008/0034478 A1 | 2/2008 | Patterson |
| 2008/0041113 A1 | 2/2008 | Mori et al. |
| 2009/0031582 A1 | 2/2009 | Lu |
| 2009/0076625 A1 | 3/2009 | Groves et al. |
| 2009/0132056 A1 | 5/2009 | Kania |
| 2009/0158504 A1 | 6/2009 | Sparrow et al. |
| 2011/0191942 A1 | 8/2011 | Villalobos |
| 2011/0277218 A1 | 11/2011 | Padilla et al. |
| 2012/0167276 A1 | 7/2012 | Brosie et al. |
| 2012/0324961 A1 | 12/2012 | Clemendot |
| 2014/0304895 A1 | 10/2014 | Stuart |
| 2014/0311187 A1 | 10/2014 | Amarasiriwardena et al. |
| 2015/0033447 A1 | 2/2015 | Riaz |
| 2015/0264995 A1 | 9/2015 | Hilderbrand, IV |
| 2016/0120233 A1 | 5/2016 | Van Tiel et al. |
| 2016/0278442 A1 | 9/2016 | Moran |
| 2016/0340813 A1 | 11/2016 | Amis et al. |
| 2017/0000216 A1 | 1/2017 | Dua et al. |
| 2017/0035120 A1 | 2/2017 | Ramsey et al. |
| 2017/0216058 A1 | 8/2017 | Dias et al. |
| 2017/0273363 A1 | 9/2017 | Patchin et al. |
| 2017/0295851 A1 | 10/2017 | Thibodeau |
| 2017/0311650 A1 | 11/2017 | Hupperets et al. |
| 2019/0029331 A1 | 1/2019 | Field |
| 2019/0104780 A1 | 4/2019 | Pinto Rodrigues |
| 2020/0080242 A1* | 3/2020 | Dardinski ................ D04B 7/32 |
| 2020/0100920 A1 | 4/2020 | Finke |
| 2020/0179140 A1 | 6/2020 | Valois et al. |
| 2020/0205484 A1 | 7/2020 | Yehuda |
| 2020/0221791 A1 | 7/2020 | Gazit et al. |
| 2020/0297514 A1 | 9/2020 | Prescott et al. |
| 2020/0308738 A1 | 10/2020 | Lineberry et al. |
| 2020/0347530 A1* | 11/2020 | Tannebaum ............. D04B 1/04 |
| 2021/0068471 A1 | 3/2021 | Giorgi et al. |
| 2021/0071329 A1 | 3/2021 | Cummings |

FOREIGN PATENT DOCUMENTS

| | | | |
|---|---|---|---|
| EP | 3330419 A1 | 6/2018 | |
| FR | 2879405 B1 | 4/2007 | |
| GB | 2271923 A | 5/1994 | |
| JP | 2007-239129 A | 9/2007 | |
| JP | 2009-97122 A | 5/2009 | |
| WO | 2004/052132 A1 | 6/2004 | |
| WO | 2007/031790 A2 | 3/2007 | |
| WO | 2012/006654 A1 | 1/2012 | |
| WO | 2012/160834 A1 | 11/2012 | |
| WO | 2018/226194 A1 | 12/2018 | |
| WO | 2019/028347 A1 | 2/2019 | |

OTHER PUBLICATIONS

Above-Knee Amputee Prosthetic Brim Sheath by GlideWear. Protects Skin from Irritation, Rubbing, Pain, GlideWear, amazon.com, ASIN: B01A5U0G2Q, Nov. 25, 2020, 4 pages.

Ez Sox Toddler Boys Socks Non Skid Anti Slip Grip Seamless Toe Pull Up Loops, Ez Sox, Amazon, ASIN: B01HPAA3G8, Available online at: <https://www.amazon.com/Ez-Sox-Toddler-Boys-Seamless/dp/B01HPAA3G8>, Accessed on Apr. 11, 2019, pp. 1-9.

(56) References Cited

OTHER PUBLICATIONS

Five Things to Know About Nike's New NBA Socks, Nike News, nike.com, Available on Internet at: <https://web.archive.or g/web/20170930140827/hllps://news.nike.com/news/nba-socks>, Sep. 15, 2017, 11 pages.
Guardian Liner, ALPS&trade, Available online at: <https://easyliner.jp/wp-content/uploads/2018/09/Guardian-Liner_EN.pdf>, Nov. 25, 2020, 2 pages.
Home: TRUSOX®—Performance Enhancing Socks, Trusox, trusox.com, Available on Internet at: <https:// web.archive.org/web/20130814050226/http://www.trusox.com>, Aug. 14, 2013, 2 pages.
Liner—Cushion Smart Seal—Above Knee, ALPS™, amputeedepot.com, Available online at: <https://amputeedepot.com/products/alps-smart-seal-cushion-liner-above-knee>, Nov. 25, 2020, 5 pages.
Ronnox Women's Cushioned Anti-Skid Non-Slip Silicone-Gripper Socks, for Yoga Pilales & Barre (Fits Women's Shoe Size 8-14), Amazon, amazon.com, ASIN: B071W2JXXR, Available on Internet at :<htlps://www.amazon.com/dp/B071W2JX XR>, Oct. 26, 2017, 5 pages.
Socks With Loops, Active Hands, Available online at: <https://www.activehands.com/product/socks-with-loops/>, Accessed on Apr. 11, 2019, pp. 1-4.
Stella McCartney: Black Loop Sock Sneakers, SSense, 191471F127002, Available online at: <ssense.com>, Accessed on Apr. 11, 2019, pp. 1-6.
ToeSox—Low Rise Grip Socks, T8 Fitness, Available online at: <https://www.t8fitness.com/products/toesox-low-rise-grip-socks>, Accessed on Apr. 11, 2019, pp. 1-2.
Valor Amputee Sock—Below Knee Mid-Volume Swiftwick, atlantacycling.com, Available online at: <https://www.atlantacycling.com/product/swiftwick-valor-amputee-sock-below-knee-mid-volume-302001-1.htm>, Nov. 25, 2020, 3 pages.
International Search Report and Written Opinion received for PCT Patent Application No. PCT/US2021/059939, dated May 6, 2022, 21 pages.
International Search Report and Written Opinion for PCT application No. PCT/US2021/059928, dated Feb. 25, 2022, 19 pages.
International Search Report and Written Opinion received for PCT Patent Application No. PCT/US2021/059920, dated Feb. 22, 2022, 16 pages.
Invitation to Pay Additional Fees received for PCT Patent Application No. PCT/US2021/059939, dated Mar. 14, 2022, 15 pages.
International Preliminary Report on Patentability received for PCT Patent Application No. PCT/US2021/059920, dated Feb. 7, 2023, 9 pages.
Non-Final Office Action received for U.S. Appl. No. 17/525,640, dated Feb. 28, 2023, 17 pages.
International Preliminary Report on Patentability received for PCT Patent Application No. PCT/US2021/059928 dated Jul. 13, 2023, 12 pages.
International Preliminary Report on Patentability received for PCT Patent Application No. PCT/US2021/059939 dated Jul. 13, 2023, 13 pages.
Notice of Allowance received for U.S. Appl. No. 17/525,640, dated Sep. 7, 2023, 12 pages.

* cited by examiner

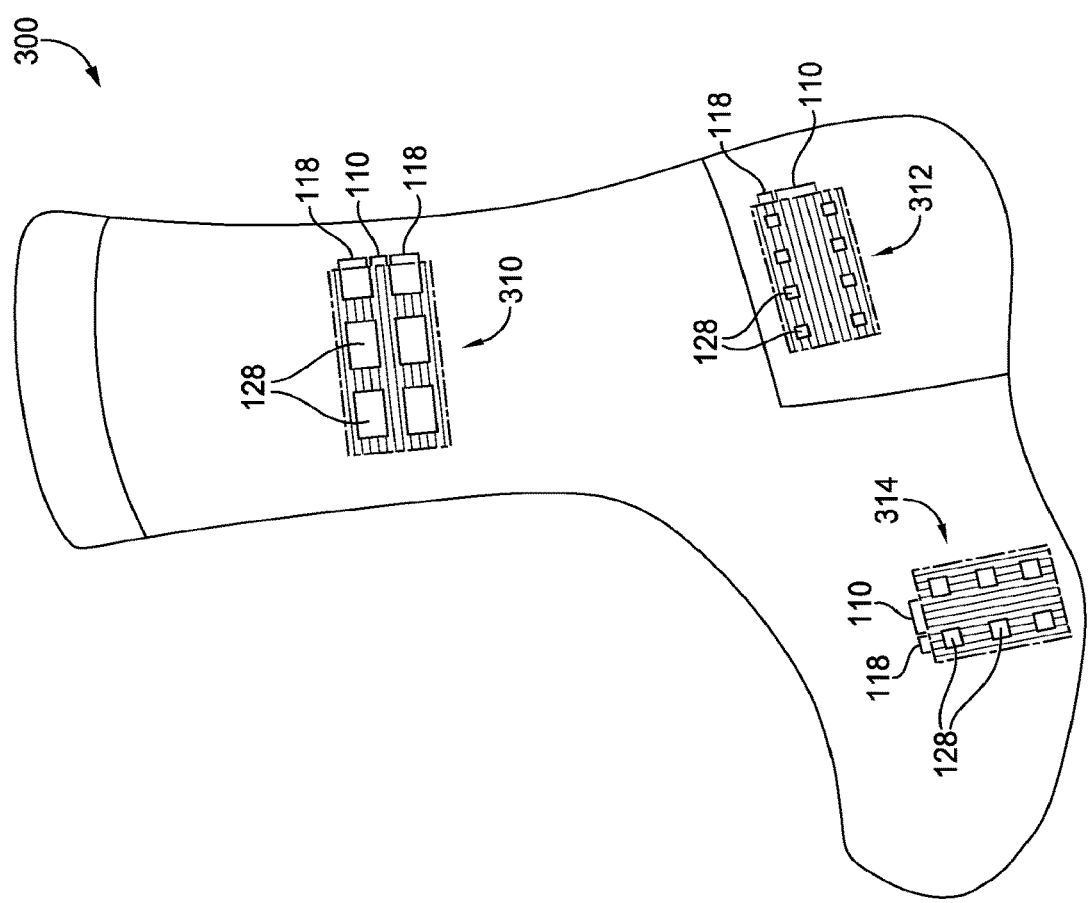
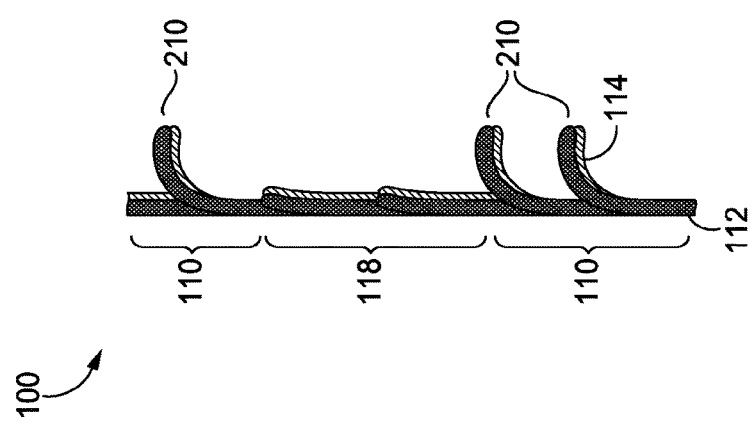
FIG. 3
FIG. 2

KNIT ARTICLE WITH VARIABLE FEATURES

CROSS-REFERENCE TO RELATED APPLICATIONS

This application, titled "Knit Article with Variable Features," claims the benefit of priority of U.S. App. No. 63/164,677, filed Mar. 23, 2021, and titled "Knit Article with Variable Features," U.S. App. No. 63/157,890, filed Mar. 8, 2021, and titled "Athletic Sock," and U.S. App. No. 63/132,593, filed Dec. 31, 2020, and titled "Sleeve for an Extremity." The entireties of the aforementioned applications are incorporated by reference herein.

TECHNICAL FIELD

Aspects herein relate to a knit structure used to form a knit article where the knit structure can be modified to impart variable cushioning, insulation, fit, breathability, and tactile feedback features to the knit article.

BACKGROUND

Traditional knit structures used to form knit articles may have a uniform construction or knitting pattern. As such, the resulting knit article may lack, for instance, zoned cushioning, zoned insulation, zoned fit, zoned tactile feedback, and/or zoned permeability/breathability features. Moreover, if the knit article includes a zoned feature in a certain location of the knit article, such as, for example, a heel area of a sock, the knit structure is generally uniform in that location such that the feature is generally uniform in that location (e.g., uniform cushioning).

BRIEF DESCRIPTION OF THE DRAWINGS

Examples of aspects herein are described in detail below with reference to the attached drawing figures, wherein:

FIG. 2 illustrates a sectional view of the example knit structure of FIG. 1 with terry loops formed on a technical back of the example knit structure in accordance with aspects herein;

FIG. 3 illustrates a view of a first side of a sock having the example knit structure of FIG. 1 in accordance with aspects herein;

DETAILED DESCRIPTION

Figure 1:
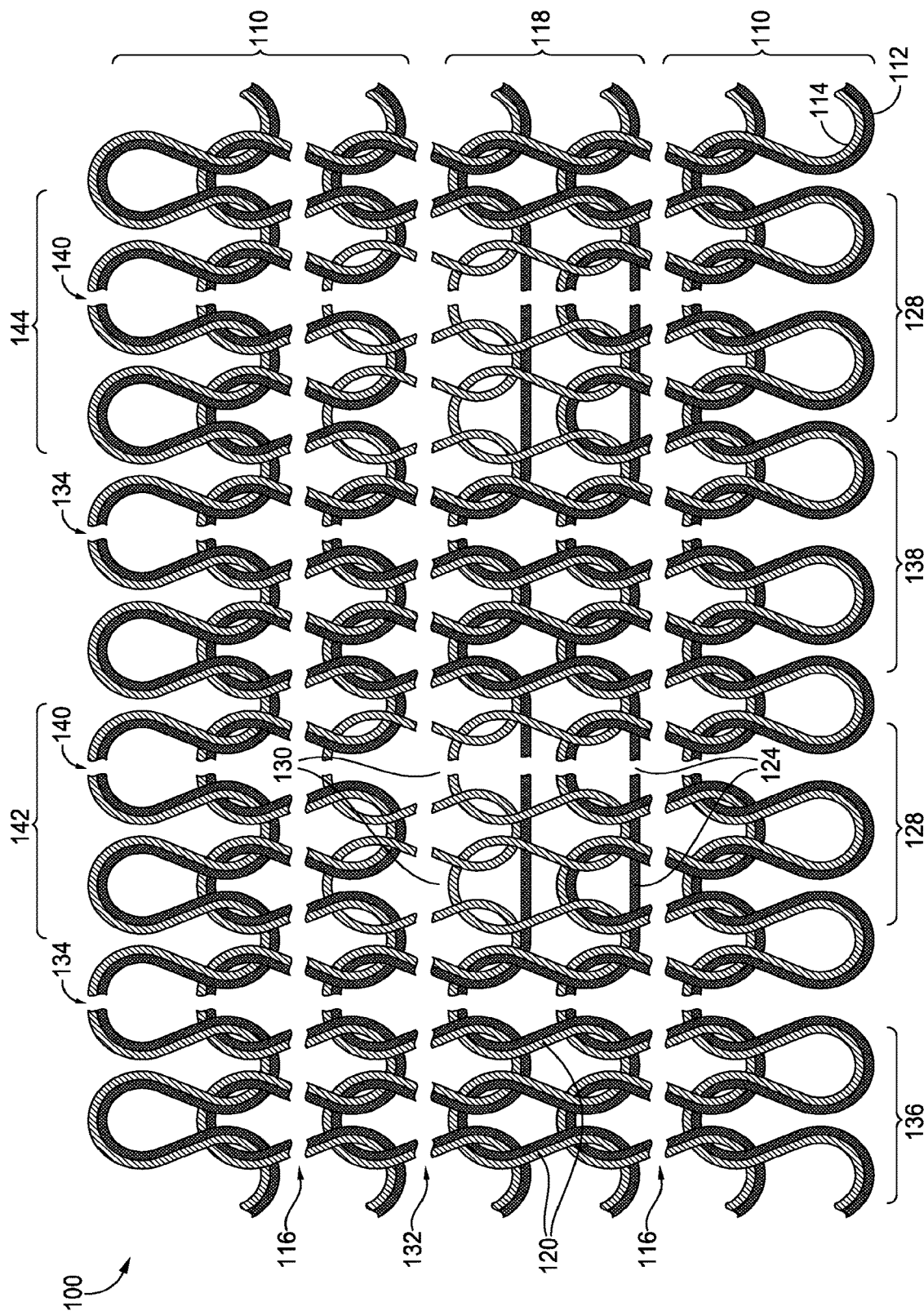
FIG. 1 illustrates an example knit structure with break lines at various locations to illustrate different ways that the knit structure can be modified in accordance with aspects herein.

The subject matter of the present invention is described with specificity herein to meet statutory requirements. However, the description itself is not intended to limit the scope of this disclosure. Rather, the inventors have contemplated that the claimed or disclosed subject matter might also be embodied in other ways, to include different steps or combinations of steps similar to the ones described in this document, in conjunction with other present or future technologies. Moreover, although the terms "step" and/or "block" might be used herein to connote different elements of methods employed, the terms should not be interpreted as implying any particular order among or between various steps herein disclosed unless and except when the order of individual steps is explicitly stated.

Traditional knit structures used to form knit articles may have a uniform construction or knitting pattern. As such, the resulting knit article may lack, for instance, zoned cushioning, zoned insulation, zoned fit, zoned tactile feedback, and/or zoned permeability/breathability features. Moreover, if the knit article includes a zoned feature in a certain location of the knit article, such as, for example, a heel area of a sock, the knit structure is generally uniform in that location such that the feature is generally uniform in that location (e.g., uniform cushioning).

Aspects herein are directed to a knit structure used to form a knit article where the knit structure can be adjusted or modified to provide zoned cushioning, zoned insulation, zoned fit, zoned permeability/breathability features, and/or zoned tactile feedback features. At a high level, the knit structure has a repeating pattern of a first number of knit courses having a first yarn knit with a first basic knit stitch and a second number of knit courses, where within each knit course of the second number of knit courses, the first yarn is knit in a repeating pattern having a first number of knit stitches knit with a second basic knit stitch and a second number of float stitches that form float areas. In example aspects, the first basic knit stitch includes terry loops and the second basic knit stitch does not include terry loops (i.e., is knit without terry loops).

Different parameters associated with the knit structure can be adjusted to provide more or less cushioning, more or less insulation, more or less breathability/permeability, more or less fit, more or less tactile feedback, and the like. For instance, greater cushioning and/or insulation may be achieved in the knit article by increasing the first number of knit courses that include the first basic knit stitch with terry loops while less cushioning and/or insulation may be achieved by decreasing the first number of knit courses that include the first basic knit stitch.

Because the first yarn is not interlooped with another knit stitch in the float areas, there is less yarn density in the float areas. Thus, greater permeability/breathability may be achieved by increasing the second number of knit courses to increase the number of the float areas and/or the size of the float areas in the walewise direction. Greater permeability/breathability may also be achieved by increasing the length of the float stitches within a given number of knit courses to increase the size of the float areas in the coursewise direction within the given number of knit courses. Conversely, less permeability/breathability may be achieved by decreasing the second number of knit courses and/or by decreasing the length of the float stitches within the given number of knit courses.

Greater tactile feedback may be achieved by, for example, using an elastic yarn as the first yarn. In one example aspect, the use of an elastic yarn in the second number of knit courses and particularly the float areas causes a "dimpling" of the knit article as the recovery properties of the elastic yarn pulls or tensions the edges of the float areas toward each other. When the knit article is worn, the dimpled areas may be positioned adjacent to a skin surface for which tactile feedback is desired such as, for example, the ball and/or heel area of a wearer's foot since these areas typically experience a high amount of contact with a ground surface. Greater tactile feedback may be achieved, for instance, by increasing the second number of knit courses in the knit structure and/or by increasing the length of the float stitches.

Because the first yarn is not interlooped with another knit stitch in the float areas, there is less yarn length in the float areas. This in turn, reduces the amount of stretch in the float areas and creates a tighter fit. Thus, a tighter fit (i.e., a greater resistance to stretch) can be achieved in areas of the knit article by increasing the number or size of the float areas in the knit article. This is accomplished by increasing the second number of knit courses and/or by increasing the length of the float stitches within a given number of courses. A more relaxed fit can be achieved in areas of the knit article by decreasing the number of the float areas in the knit article. This can be accomplished by decreasing the second number of knit courses and/or by decreasing the length of the float stitches within a given number of courses.

Parameters of the knit structure may also be adjusted along a particular set of courses. For example, with respect to the second number of knit courses, the length of the float stitches may be adjusted to different lengths along a particular set of courses to adjust the permeability/breathability features, the fit features, and/or the tactile feedback features along the lengthwise direction of the courses.

The term "knit structure" as used herein refers to a textile produced during a single knitting event. Aspects herein contemplate that the knit structure may be formed through a weft knitting process including, for example, circular knitting and flat knitting processes. The knit structure may be used to form one or more knit articles. The term "knit article" as used herein refers to any type of article that may be worn by a wearer including, for example, upper-body garments, lower-body garments, extremity sleeves (e.g., calf sleeves, arm sleeves), socks, uppers for shoes, gloves, hats, and the like. Positional terms as used herein to describe a knit article are with respect to the knit article being worn as intended by a wearer standing upright. The term "inner-facing surface" means the surface of the knit article that is configured to face toward a skin surface of a wearer. In example aspects, the inner-facing surface may be the innermost-facing surface of the knit article. The term "outer-facing surface" means the surface of the knit article that faces away from the inner-facing surface and toward an external environment. In example aspects, the outer-facing surface may be the outermost-facing surface of the knit article. In example aspects, the inner-facing surface may comprise the technical back of the knit article and the outer-facing surface may comprise the technical front of the knit article.

The term "knit course" as used herein refers to a predominantly horizontal row of knit loops (in an upright textile as knit) that are produced by adjacent needles during the same knitting cycle. The knit course may comprise one or more stitch types such as a knit stitch, a held stitch, a float stitch, a tuck stitch, a transfer stitch, and the like as these terms are known in the art of knitting. The term "wale" as used herein is a predominantly vertical column of intermeshed or interlooped knit loops, generally produced by the same needle at successive (but not necessarily all) courses or knitting cycles. The terms "horizontal" and "vertical" are relative to an upright textile as knit in which the heads of knit loops face toward the top of the textile and the course knit first is oriented toward the bottom of the textile. The term "coursewise direction" refers to a direction parallel to the direction of the knit courses. The term "walewise direction" refers to a direction orthogonal to the direction of the knit courses and/or parallel to the direction of the wales.

The term "first basic knit stitch" as used herein refers to the basic stitch type where a loop of yarn is pulled from the technical back of the knit article to the technical front through a previous stitch. Thus, the legs of the stitch appear on the technical face of the knit article and the top and bottom of the stitch appear on the technical back of the knit article. As used herein, the first basic knit stitch includes terry loops. The term "terry loops" refers to loops formed from knit yarns that extend away from the technical face and/or the technical back of a knit article and is to be given the meaning that is commonly used in the art of knitting. In example aspects, the terry loops extend away from the technical back of the knit article such that they face toward a skin surface of a wearer. The term "second basic knit stitch" as used herein refers to the basic stitch type where a loop of yarn is pulled from the technical back of the knit article to the technical front through a previous stitch, but the second basic knit stitch does not include terry loops (i.e., the yarn is knit without terry loops). The term "float stitch" as used herein occurs when no new stitch is formed at a needle. Thus, the float yarn may extend across one or more adjacent wales. When describing that a first location of a knit article may have a "greater number of float stitches" than a second location, this may mean that the float stitch extends over a greater number of wales in the first location compared to the second location. The term "plating" as used herein means a knit construction where one or more body yarns (i.e., first yarns) and one or more plating yarns (i.e., second yarns) are knit in the same knit stitch using, for instance, a body yarn feeder and one or more plating yarn feeders.

The yarns used to form the knit article may include yarns formed from natural fibers/filaments (e.g., cotton, wool, silk, and the like), yarns that includes synthetic fibers/filaments (e.g., polyester, nylon, and the like), or yarns that contains both natural fiber/filaments and synthetic fibers/filaments. The yarns used to form the knit article may also include elastic yarns where the term "elastic" refers to the yarn's ability to stretch to about 100% to about 200% of its original length and recover to approximately (e.g., within 5% to 10%) its original length after the stretching force is removed. In example aspects, the elastic yarn may be covered with other yarns such as polyester or nylon yarns. The term "integrally knit" as used herein may mean a knit article having a yarn from one or more knitted courses being interlooped with one or more knitted courses of another area. The knit article may be integrally knit during a single knitting event although cut-and-sew constructions are also contemplated herein.

The term permeability is the measure of air flow passed through a given area of the knit structure and may be measured using ASTM D737 testing methods. The term breathability as used herein is the ability of the knit structure to allow moisture vapor to be transmitted through the material and may be measured, for example, using ASTM E96 testing methods.

Unless indicated otherwise, all measurements provided herein are taken when the knit article is at standard ambient temperature and pressure (298.15 K and 100 kPa) and the knit article is in a resting state (e.g., an unstretched state).

FIG. 1 illustrates an example knit structure 100 that may be used to form a knit article where the knit structure 100 is knit using at least a first yarn 112 (shown with cross-hatching) and optionally a second yarn 114 (shown with hatching) where the first yarn 112 and the second yarn 114 (when used) are in a plated relationship. The knit structure 100 may include additional plated yarns. The knit structure 100 depicts a portion of a repeating patterns that includes a first number of knit courses 110 integrally knit with a second number of knit courses 118. Thus, the pattern includes the first number of knit courses 110, the second number of knit courses 118, the first number of knit courses 110, the second number of knit courses 118, and so on. Thus, there may be multiple sets of the first number of knit courses 110 and multiple sets of the second number of knit courses 118.

In example aspects, the first number of knit courses 110 are knit with a first basic knit stitch. As shown in FIG. 2 discussed below, the first yarn 112 and optionally the second yarn 114 are knit to form terry loops on the technical back of the knit structure 100. The terry loops provide cushioning as well as insulation due to air trapping in the yarn loops. They may also provide increased stretch properties due to the extra yarn length in the terry loops. In example aspects, the first yarn 112 may include different deniers depending on a desired functional benefit. For instance, higher denier yarns may be used to achieve increased cushioning and/or insulation compared to yarns with a smaller denier. The first yarn 112 may be elastic or non-elastic. In example aspects, the second yarn 114 may include an elastic yarn or a non-elastic yarn. An elastic second yarn 114 may be used in knit articles such as, for example, socks or extremity sleeves to provide stretch and recovery and to help maintain the knit article in a fixed position on the wearer.

Break lines 116 are depicted to illustrate that the first number of knit courses 110 may include additional knit courses not shown. In example aspects, the first number of knit courses 110 may include from about two knit courses to about ten knit courses. A greater number of knit courses 110 may be used when increased cushioning, insulation, and/or stretch is desired due to the increased number of terry loops. Conversely, a fewer number of knit courses 110 may be used when decreased cushioning, insulation, and/or stretch is desired.

The knit structure 100 further includes the second number of knit courses 118. The second number of knit courses 118 includes a repeating pattern of a first number of knit stitches, referenced generally by the numeral 120, knit with a second basic knit stitch without terry loops and a second number of float stitches, referenced generally by the numeral 124, to form float areas 128. In example aspects, when the second yarn 114 is used, the second yarn 114 may be continuously knit with the second basic knit stitch in the second number of knit courses 118 including in the float areas 128 as indicated by reference numeral 130. Continuously knitting the second yarn 114 in the second number of knit courses 118 may help provide structure and stability to the knit article. In further example aspects, when the second yarn 114 is used, the first yarn 112 may float on the technical back of the knit structure 100 in the float areas 128 as shown. Within the second number of knit courses 118, the first number of knit stitches 120 are aligned in a walewise direction and the second number of float stitches 124 are aligned in the walewise direction. Although FIG. 1 depicts the first number of knit stitches 120 being a same number as the second number of float stitches 124, it is contemplated herein that the first number of knit stitches 120 may be a different number than the second number of float stitches 124.

As depicted, the float areas 128 have less yarn density due to the float stitches 124 as compared to areas knit with the first basic knit stitch and the second basic knit stitch. Stated differently, because the first yarn 112 is not interlooped with other knit stitches in the float areas 128, there is less yarn present in the float areas 128. This, in turn, increases the permeability and/or the breathability of the knit structure 100 in the float areas 128. Further, because the first yarn 112 is not interlooped with other knit stitches in the float areas 128, the length of the first yarn 112 is decreased in the float areas 128 compared to the non-float areas of the knit structure 100. Because there is less yarn length in the float areas 128, there is a greater resistance to stretch, including mechanical stretch, which may create a tighter fit.

When the first yarn 112 is an elastic yarn, the recovery properties of the first yarn 112 may cause a dimpling or three-dimensional (3-D) deformation of the knit structure 100 as the edges of the float areas 128 are drawn toward each other causing the float areas 128 to extend in a z-direction with respect to a surface plane of the knit structure 100. In example aspects, when the first yarn 112 is floated on the technical back of the knit structure 100, the float areas 128 extend toward a skin surface of a wearer. The dimpling or 3-D deformation of the knit structure 100 may provide a tactile feedback feature to the knit article. For example, the dimpled areas of the knit article may be positioned adjacent to an area of a wearer for which tactile feedback is desired such as, for example, areas of the foot, the back of a wearer, and the like.

A break line 132 is depicted to illustrate that the second number of knit courses 118 may include additional knit courses not shown. In example aspects, the second number of knit courses 118 may include from about two knit courses to about fourteen knit courses depending on knitting machine capabilities. A greater number of knit courses 118 within a given set of knit courses 118 increases the size of the float areas 128 in the walewise direction, which may increase the permeability and/or breathability features of the knit structure 100. Conversely, a fewer number of knit courses 118 within a given set of knit courses 118 decreases the size of the float areas 128 in the walewise direction, which may reduce the permeability and/or breathability features of the knit structure 100.

Break lines 134 are depicted to illustrate that the first number of knit stitches 120 may include additional knit stitches not shown. In example aspects, the first number of knit stitches 120 may include from two knit stitches to ten knit stitches (or greater), from two knit stitches to eight knit stitches, from two knit stitches to six knit stitches, or from two knit stitches to four knit stitches. Increasing the first number of knit stitches 120 reduces the number of float areas 128 within the second number of knit courses 118 for a resulting knit article. This, in turn, may decrease the permeability and/or breathability of the resulting knit article. Additionally, it may create a greater degree of stretch in the resulting knit article due to the increased number of yarn loops.

It is further contemplated herein, that a first set 136 of the first number of knit stitches 120 may include the same or a different number of knit stitches than a second set 138 of the first number of knit stitches 120. Stated differently, the first number of knit stitches 120 may vary or stay the same along the second number of knit courses 118 depending on a desired attribute.

Break lines 140 are depicted to illustrate that the second number of float stitches 124 may extend over a greater number of wales. In example aspects, the second number of float stitches 124 may extend over two wales to ten wales, over two wales to eight wales, over two wales to six wales, or over two wales to five wales. Extending the second number of float stitches 124 over a greater number of wales increases the size or surface area of the float areas 128 in the coursewise direction. This, in turn, may increase the permeability and/or breathability of the knit structure 100. Additionally, it may create a greater resistance to stretch in the knit structure 100. In example aspects, it may be desirable not to extend the second number of float stitches over more than, for example, ten wales to reduces incidences of snagging.

It is additionally contemplated herein, that a first set 142 of the second number of float stitches 124 may include the same or a different number of float stitches than a second set 144 of the second number of float stitches 124. Stated differently, the second number of float stitches 124 may vary or stay the same along a given set of the second number of knit courses 118 depending on a desired attribute.

Varying the first number of knit stitches 120 and the second number of float stitches 124 allows for a feature to be adjusted at different locations along the coursewise direction of a given set of the second number of knit courses 118. For example, if increased breathability/permeability is desired in a certain location along a given set of the second number of knit courses 118, the second number of float stitches 124 may be increased relative to the first number of knit stitches 120 in that location such that the second number of float stitches 124 extend over a greater number of wales. The converse is true if decreased breathability/permeability is desired in the location. If a greater resistance to stretch is desired in a certain location along a given set of the second number of knit courses 118, the second number of float stitches 124 may be increased relative to the first number of knit stitches 120 in that location. The converse is true if a decreased resistance to stretch is desired in that location. Tactile feedback may be adjusted at locations along a given set of the second number of knit courses 118 by increasing or decreasing the length of the float stitches 124 in desired locations and/or by making the first yarn 112 an elastic yarn.

FIG. 2 illustrates a sectional view of the example knit structure 100. As shown, in the first number of knit courses 110, the first yarn 112 and optionally the second yarn 114 are knit in the first basic knit stitch to form terry loops 210 on the technical back of the knit structure 100. The extra volume of yarn in the terry loops 210 helps to provide cushioning where used and may provide increased stretch properties. Additionally, the terry loops 210 may help to trap air and provide insulation. In the second number of knit courses 118, the first yarn 112 and optionally the second yarn 114 are knit in the second basic knit stitch that does not form terry loops. As further shown in FIG. 2, the first number of knit courses 110 are integrally knit with the second number of knit courses 118.

FIG. 3 depicts an example knit article in the form of a sock 300 that utilizes the example knit structure 100. Portions of the knit structure 100 are schematically depicted at various locations on the sock 300 such that the float areas 128 are indicated by boxes and knit courses are represented by lines. The sock 300 includes location 310 positioned at the leg portion of the sock 300, location 312 positioned at the heel portion of the sock 300, and location 314 positioned at the forefoot portion of the sock 300.

In the location 310, the second number of knit courses 118 is greater than the first number of knit courses 110. In addition, the second number of float stitches 124 is greater in the location 310 than, for example, the locations 312 and 314. This results in the float areas 128 having an increased size in both the coursewise direction and the walewise direction than the float areas in the locations 312 and 314. As such, breathability/permeability may be greater at the location 310 compared to the locations 312 and 314. As well, there may be a greater resistance to stretch due to the larger float areas 128 at the location 310 compared to the locations 312 and 314. The greater resistance to stretch may help to maintain the leg portion of the sock 300 in a relatively fixed position on the leg of a wearer, and the increased size of the float areas 128 may allow for increased air and/or moisture exchange and provide a cooling effect for the wearer.

In the location 312, the first number of knit courses 110 is greater than the second number of knit courses 118. As such, cushioning may be increased at the location 312 compared to, for example, the location 310. Because the heel of a wearer is a high contact area with the ground, increased cushioning may be a desirable attribute. The use of the float areas 128 at the location 312 may increase the resistance to stretch and provide a more secure fit of the heel portion of the sock 300. Additionally, when an elastic yarn is used in the float areas 128, the dimpling of the knit structure may provide a tactile feedback feature in the location 312.

Increased cushioning may also be a desirable feature at the location 314 positioned at the forefoot portion of the sock 300 since this is often a high contact area of the sock 300. As such, at the location 314, the first number of knit courses 110 is greater than the second number of knit courses 118. To provide enhanced tactile feedback at this high contact area, the second number of knit courses 118 and/or the second number of float stitches 124, and thus the size of the float areas 128 in both the coursewise and the walewise direction, may be increased compared to the location 312. The positioning of the locations 310, 312, and 314 is illustrative and it is contemplated herein that features of the knit structure 100 described herein may be modified to achieve one or more desired functional effects at a desired location on a knit article such as the sock 300.

Figure 4:
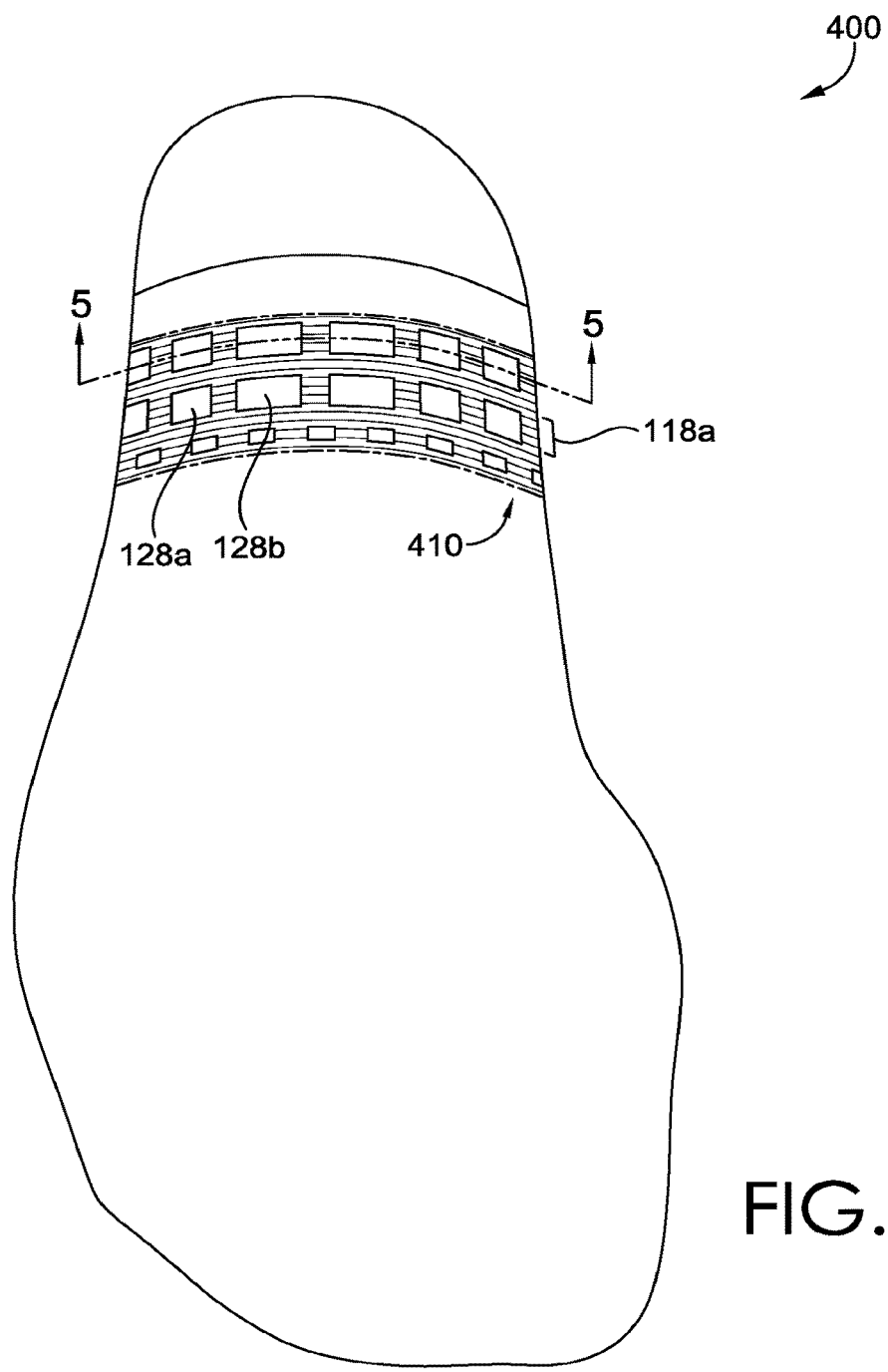
FIG. 4 illustrates a bottom view of a sock having the example knit structure of FIG. 1 in accordance with aspects herein.

FIG. 4 illustrates a bottom view of an example knit article in the form of a sock 400 with a location 410 of the knit structure 100 positioned toward the rear of the sock 400 in the heel area. FIG. 4 is provided to illustrate how the size of the float areas 128 may be varied along a given set of the second number of knit courses 118. For example, along the second number of knit courses 118a, float area 128b extends over a greater number of wales than float area 128a. The construction thus described varies breathability/permeability features, fit features, and tactile feedback features within a given location such as the location 410 shown in FIG. 4. The positioning of the location 410 is illustrative and it is contemplated herein that features of the knit structure 100 described herein may be modified to achieve desired functional effects at a desired location on a knit article such as the sock 400.

Figure 5:
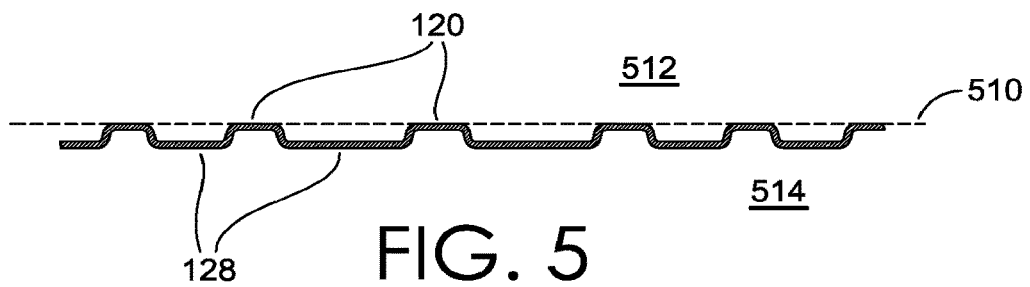
FIG. 5 illustrates a cross-section taken at cut line 6-6 of FIG. 5 and depicts dimpling of the knit article in accordance with aspects herein.

FIG. 5 is a cross-section of the sock 400 taken at cut line 5-5 of FIG. 4 and is provided to illustrate how use of elastic yarns for the first yarn 112 in the knit structure 100 causes a dimpling or 3-D deformation of the sock 400. A surface plane of the sock 400 is indicated by the dashed line 510.

The float areas 128 are shown extending in a z-direction away from the surface plane 510. The float areas 128 are generally positioned on a technical back 514 of the sock 400 and face away from a technical front 512 of the sock 400. By positioning the float areas 128 on the technical back 514, the float areas 128 extend toward a skin surface of a wearer to provide a tactile feedback feature. In example aspects, the dimpling or 3-D deformation of the sock 400 in this location may provide important sensory or tactile feedback for balance and muscle activity during locomotion.

Figure 6:
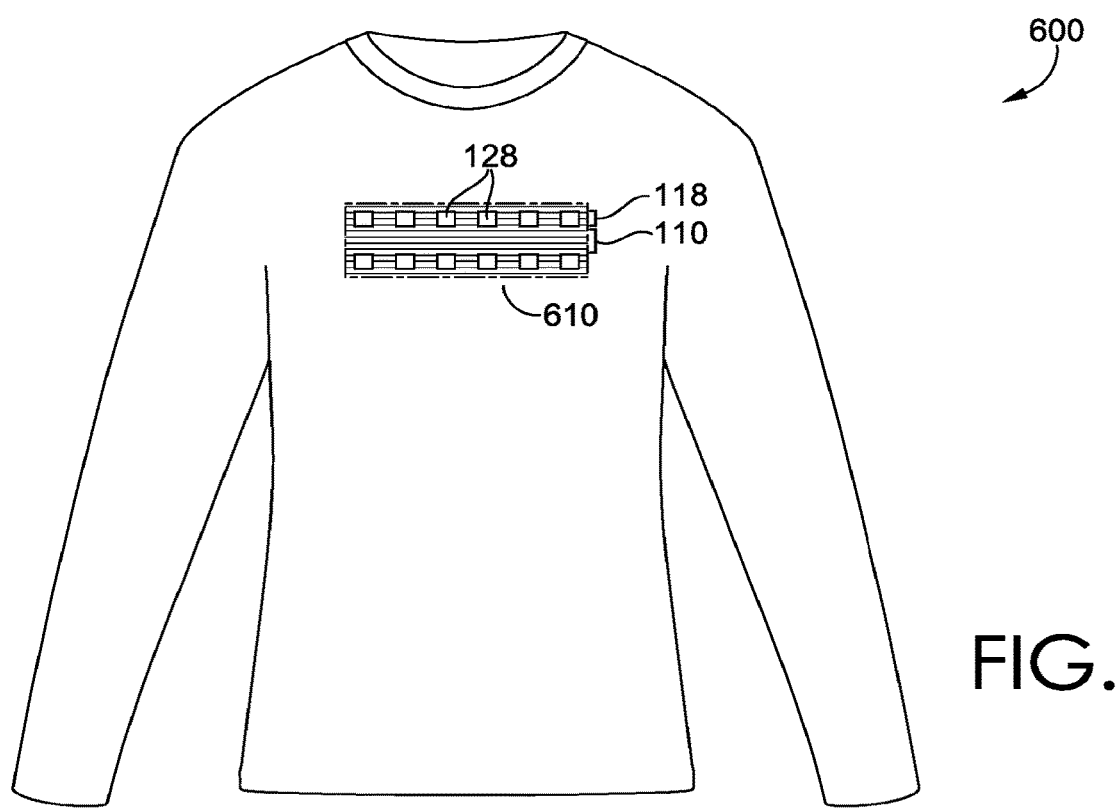
FIGS. 6-7 illustrate front and back views respectively of an example upper-body knit article having the knit structure of FIG. 1 in accordance with aspects herein.
Figure 7:
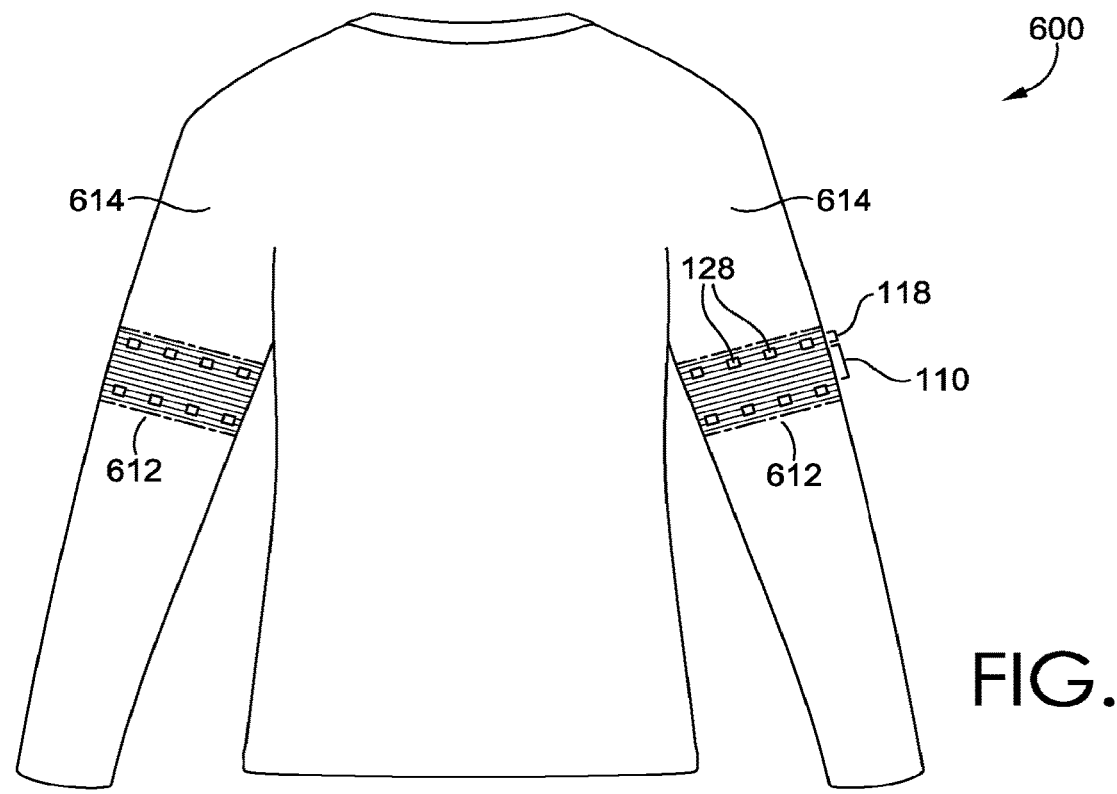

FIGS. 6-7 respectively illustrate front and back views of an example upper-body knit article 600 that is formed in whole or in part from the knit structure 100. With respect to FIG. 6, a location 610 having the knit structure 100 is depicted across an upper chest portion of the upper-body knit article 600 such that the location 610 is configured to be positioned adjacent to an upper front chest area of a wearer. With respect to FIG. 7, a location 612 having the knit structure 100 is shown on each of sleeve portions 614 of the upper-body knit article 600 such that the locations 612 are configured to be positioned adjacent to an arm area of the wearer. Comparing the location 610 with the locations 612, the float areas 128 are larger in size in both the coursewise and the walewise direction in the location 610 compared to the location 612. This may reflect that an increased level of breathability/permeability is desired in this high heat producing area of the wearer. The first number of knit courses 110 is greater in the location 612 compared to the location 610 such that there is an increased number of terry loops at the location 612 compared to the location 610. This may reflect that an increased level of insulation, cushioning, and/or stretch is desired in this area of the upper-body knit article 600. The positioning of the locations 610 and 612 is illustrative and it is contemplated herein that features of the knit structure 100 described herein may be modified to achieve desired functional effects at a desired location on a knit article such as the upper-body knit article 600.

Figure 8:
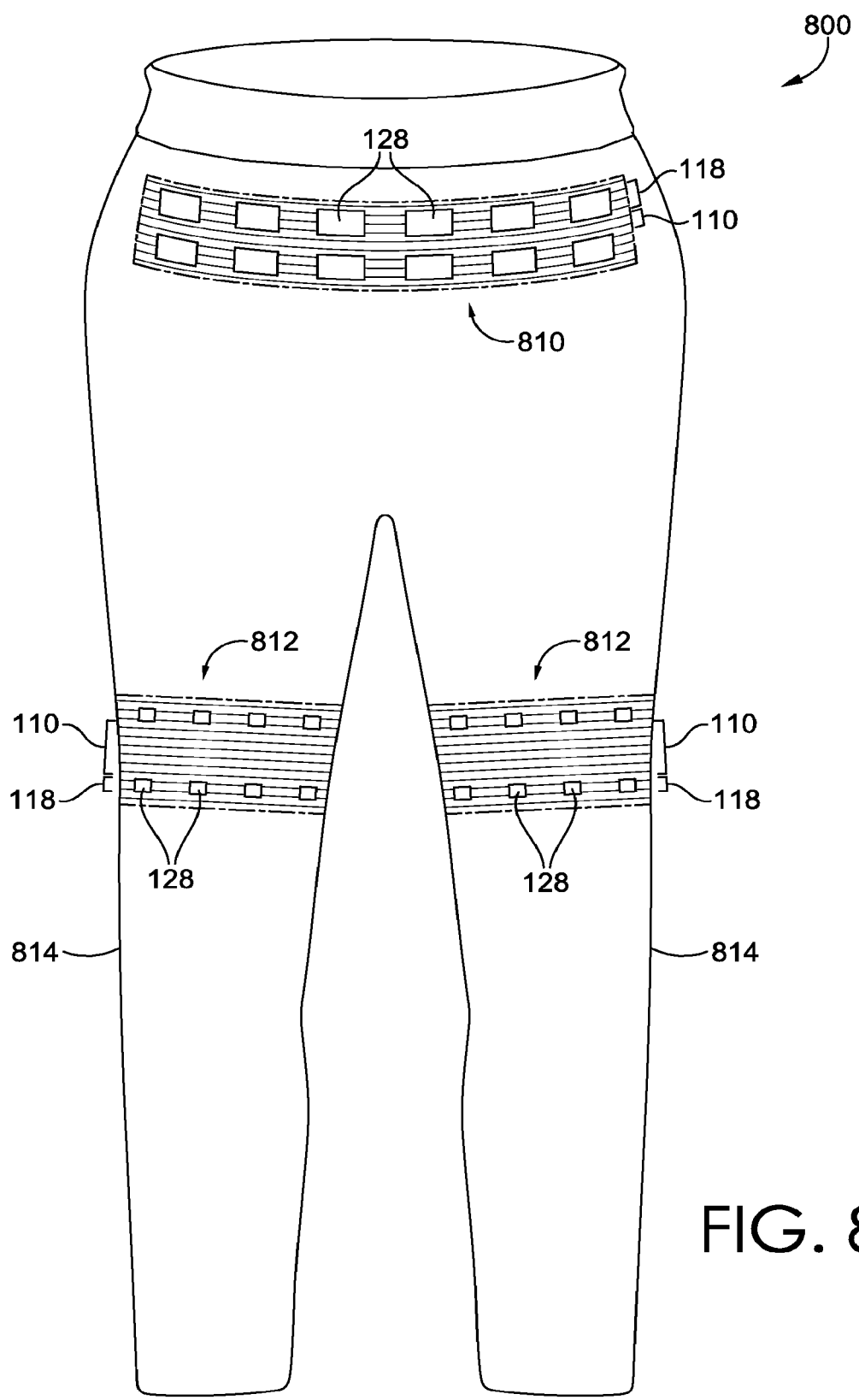
FIG. 8 illustrates a front view of an example lower-body knit article having the knit structure of FIG. 1 in accordance with aspects herein.

FIG. 8 illustrates a front view of an example lower-body knit article 800 that is formed in whole or in part from the knit structure 100. FIG. 8 depicts location 810 formed from the knit structure 100 and positioned at a front upper torso portion of the lower-body knit article 800 such that the location 810 is configured to be positioned adjacent to a front lower torso area of a wearer. FIG. 8 further depicts locations 812 formed from the knit structure 100 and positioned at a front upper part of leg portions 814 such that the locations 812 are configured to be positioned adjacent to a front thigh area of the wearer. Comparing the location 810 with the locations 812, the float areas 128 are larger in size in both the coursewise and the walewise direction in the location 810 compared to the locations 812. This may reflect that an increased level of breathability/permeability is desired in this area of the wearer. The first number of knit courses 110 is greater in the locations 812 compared to the location 810 such that there is an increased number of terry loops at the locations 812 compared to the location 810. This may reflect that an increased level of insulation, cushioning, and/or stretch is desired in this area of the lower-body knit article 800. The positioning of the locations 810 and 812 is illustrative and it is contemplated herein that features of the knit structure 100 described herein may be modified to achieve desired functional effects at a desired location on a knit article such as the lower-body knit article 800.

Figure 9:
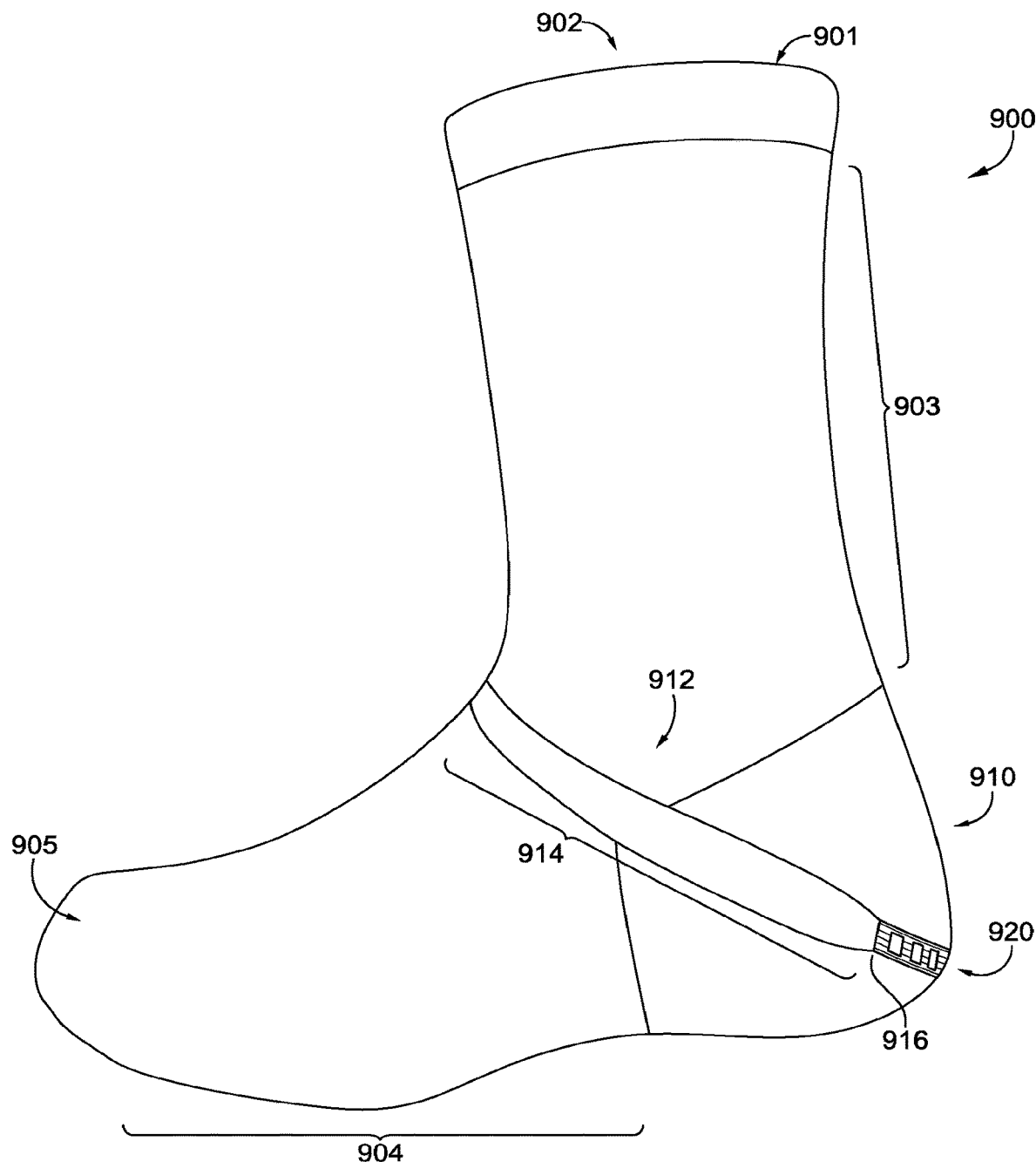
FIGS. 9-11 respectively illustrate a lateral view, a rear view, and a medial view of a sock having heel band that incorporates the example knit structure of FIG. 1 in accordance with aspects herein.
Figure 10:
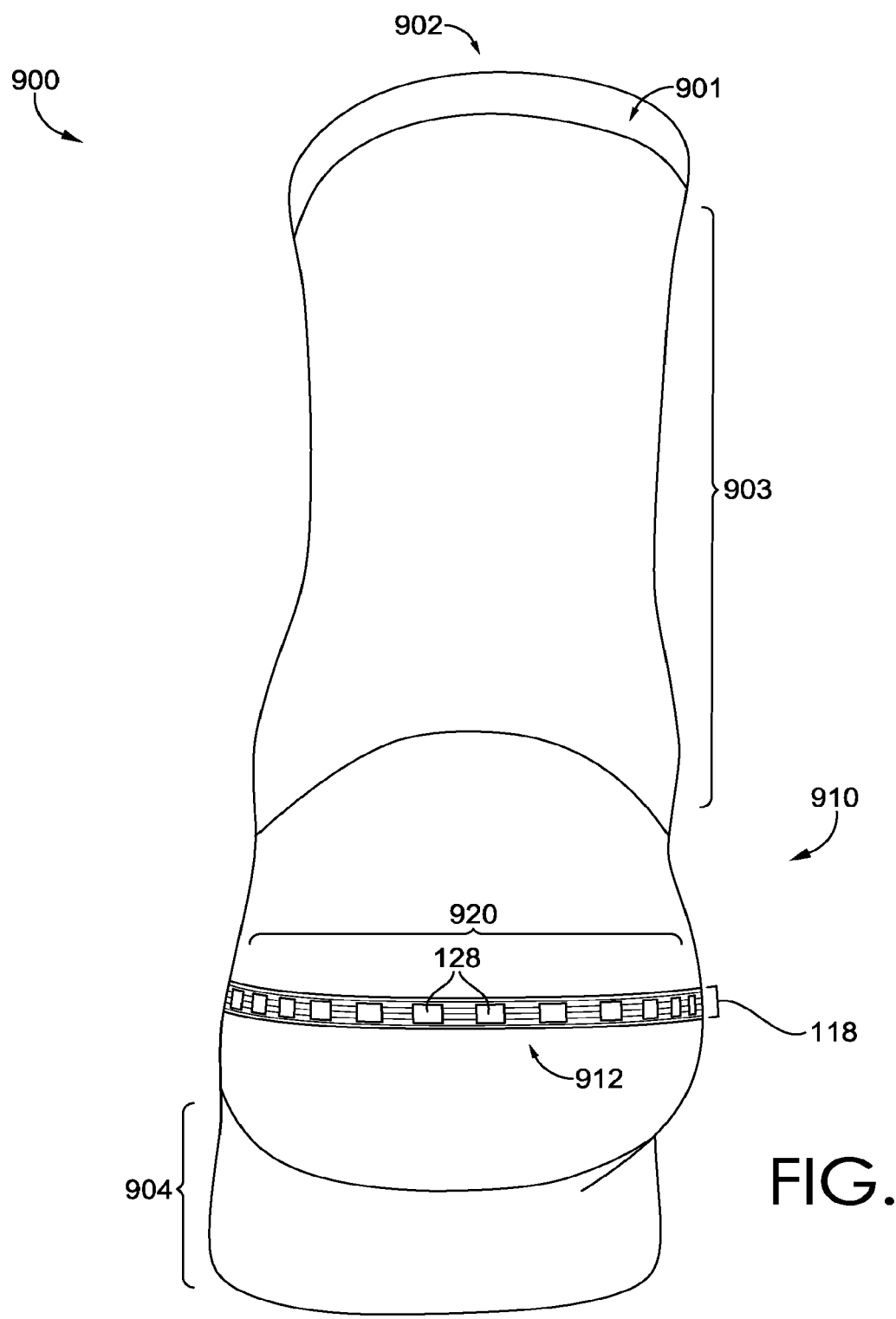
Figure 11:
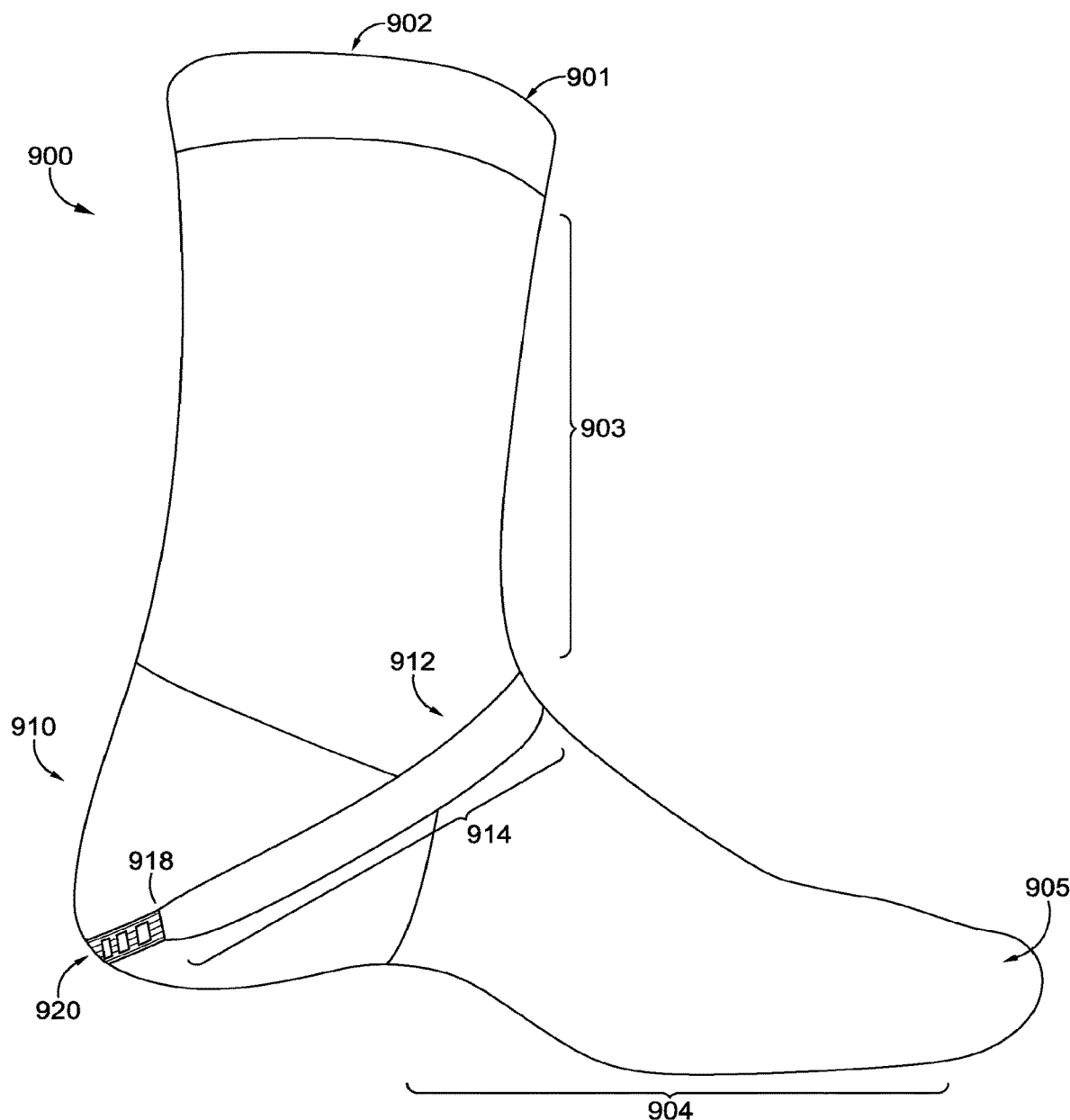

FIGS. 9-11 depict an additional example use of aspects of the knit structure 100 in a knit article such as a sock 900. FIGS. 9-11 respectively depict a lateral view, a rear view, and a medial view of the sock 900. The sock 900 includes a collar 901 having a perimeter edge around an opening 902 for receiving a wearer's foot. The sock 900 additionally includes a leg portion 903 extending from the collar 901, and a foot portion 904 extending from the leg portion 903 where the foot portion 904 terminates at a toe end 905. The sock 900 also includes a heel portion 910 positioned between the leg portion 903 and the foot portion 904 where the heel portion 910 is configured to be positioned adjacent to a heel area of a wearer when the sock 900 is worn. In example aspects, parts of the heel portion 910 (e.g., the heel pocket) may be knit using a reciprocating knitting process as is known in the art of sock knitting. To help secure the heel portion 910 against the heel area of the wearer when the sock 900 is worn, the sock 900 may further include an integrally knit heel band 912 that is knit to extend circumferentially around a lower end of the leg portion 903. Stated differently, the heel band 912 is circular knit instead of reciprocally knit.

The heel band 912 has a first portion, indicated by reference numeral 914 that includes continuous knit stitches forming a plurality of courses that extend from a first location 916 (shown in FIG. 9) positioned at a rear, lateral side of the heel portion 910, around a front aspect of the sock 900 at an ankle/instep area of the sock 900, to a second location 918 (shown in FIG. 11) positioned at a rear medial side of the heel portion 910. The first portion 914 may, in example aspects, include a high denier elastic yarn that helps to fix the heel band 912 in position and prevent shifting during wear.

The heel band 912 further includes a second portion, indicated by reference numeral 920. In example aspects, the second portion 920 extends from the first location 916 around the apex of the heel portion 910 at the rear of the heel portion 910, and to the second location 918. When the sock 900 is worn, the second portion 920 may be positioned generally at the area where the bottom part of the heel of the wearer transitions to the rear part of the heel. In example aspects, the first portion 914 in combination with the second portion 920 generally divides the heel portion 910 into a top half and a bottom half.

The second portion 920 may be knit using one or more yarns including a body yarn and one or more plating yarns (e.g., the first yarn 112 and the second yarn 114). In example aspects, each of the body yarn and the one or more plating yarns may include elastic yarns, which impart a high degree of recovery to the second portion 920. In example aspects, the second portion 920 may be knit using aspects of the knit structure 100. For example, the second portion 920 may be formed using at least the second number of knit courses 118 having the repeating pattern of the first number of knit stitches 120 and the second number of float stitches 124 that form the float areas 128.

As explained above, there is less yarn length in the float areas 128 which results in a greater resistance to stretch in the coursewise direction (i.e., in a medial-to-lateral direction in the sock 900 as worn) as compared to the first portion 914 of the heel band 912. Stated differently, since the first portion 914 of the heel band 912 does not include float stitches, there is less resistance to stretch in the medial-to-lateral direction as compared to the second portion 920 of the heel band 912. The greater resistance to stretch in the medial-to-lateral direction in the second portion 920 further helps to secure the heel band 912 in position around the rear heel of a wearer. To describe this in a different way, the first portion 914 of the heel band 912 may exhibit a first degree of stretch in the coursewise direction, and the second portion 920 of the heel band 912 may exhibit a second degree of stretch in the coursewise direction where the second degree of stretch is less than the first degree of stretch.

Aspects herein contemplate that additional areas of the heel portion 910 and/or the sock 900 may be formed from the knit structure 100 as described above with respect to, for example, the sock 300 and/or the sock 400.

The knit structure 100 described herein may be used in additional knit articles not shown such as extremity sleeves, uppers, gloves, hats, and the like. As described herein, the knit structure 100 may be adjusted at different locations or areas of the knit article to achieve a desired property such as breathability/permeability, fit, cushioning, insulation, tactile feedback, and the like.

Figure 12:
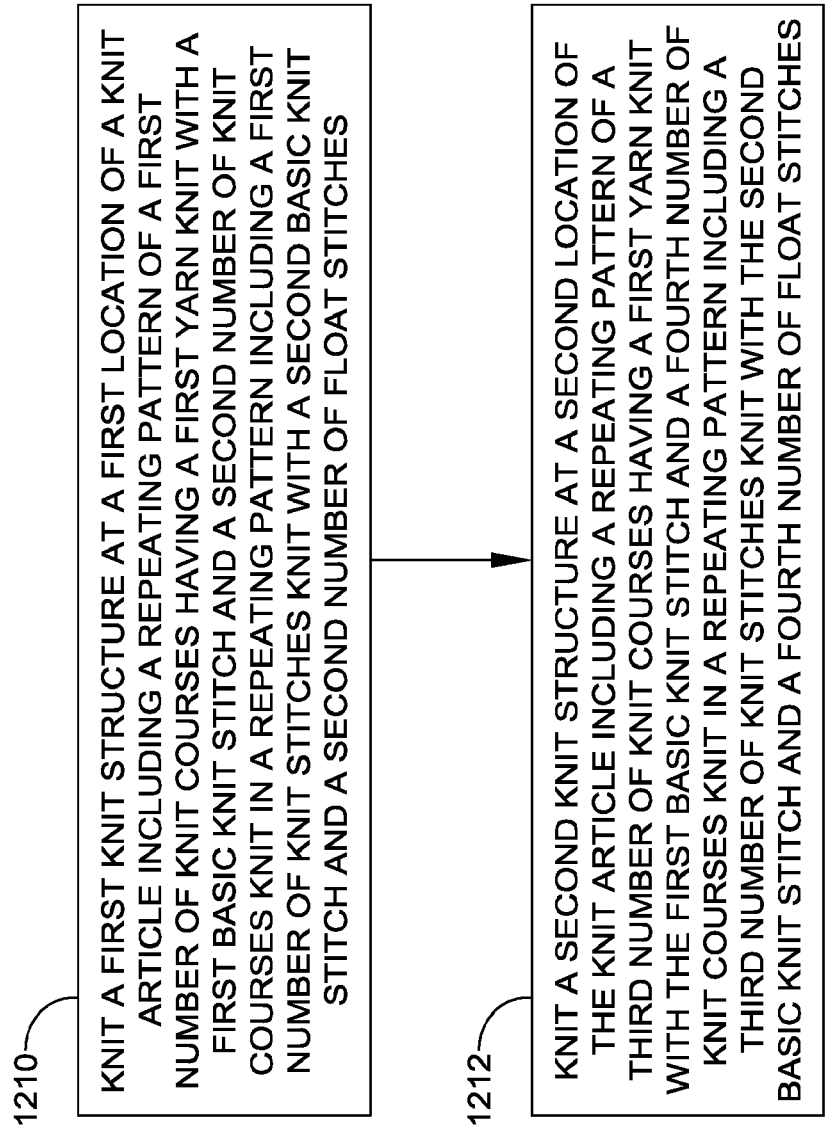
FIG. 12 illustrates a flow diagram of an example method of manufacturing a knit article in accordance with aspects herein.

FIG. 12 depicts a flow diagram of an example method 1200 of knitting a knit article such as, for example, the sock 300, the sock 400, the upper-body knit article 600, the lower-body knit article 800, and the sock 900. The method 1200 may be executed on, for instance, a circular weft knit machine or a flat weft knit machine. It is contemplated herein that the method 1200 may be executed during a single knitting event such that an integrally knit article is formed and there are minimal post-production manufacturing steps.

At a step 1210, a first knit structure such as the knit structure 100 is knit at a first location of the knit article such as the location 310 of the sock 300. The first knit structure includes a repeating pattern of a first number of knit courses, such as the first number of knit courses 110 having a first yarn knit in a first basic knit stitch with terry loops and a second number of knit courses, such as the second number of knit courses 118. The second number of knit courses are knit in a repeating pattern having a first number of knit stitches, such as the first number of knit stitches 120, knit with a second basic knit stitch without terry loops and a second number of float stitches, such as the second number of float stitches 124, to form float areas such as the float areas 128.

At a step 1212, a second knit structure is knit at a second location of the knit article, such as the location 312 of the sock 300. In example aspects, the second knit structure includes one or more modifications of the first knit structure in order to achieve a different functional effect. In example aspects, the second knit structure includes a repeating pattern of a third number of knit courses having the first yarn knit in the first basic knit stitch with terry loops and a fourth number of knit courses. The fourth number of knit courses are knit in a repeating pattern having a third number of knit stitches knit with the second basic knit stitch without terry loops and a fourth number of float stitches to form float areas. In example aspects, one or more of the third number of knit courses is different from the first number of knit courses, and the fourth number of float stitches is different from the second number of float stitches. In further example aspects, one or more of the fourth number of knit courses is different from the second number of knit courses and the third number of knit stitches is different from the first number of knit stitches. Any and all aspects, and any variation thereof, are contemplated as being within aspects herein.

With respect to the method 1200, in example aspects, the first and second knit structures may also include one or more additional yarns, such as the second yarn 114 that are knit in a plated relationship with the first yarn. Within the second number of knit courses, it is contemplated that the second yarn may be continuously knit such that float areas include the second yarn knit in the second basic knit stitch without terry loops.

The following clauses represent example aspects of concepts contemplated herein. Any one of the following clauses may be combined in a multiple dependent manner to depend from one or more other clauses. Further, any combination of dependent clauses (clauses that explicitly depend from a previous clause) may be combined while staying within the scope of aspects contemplated herein. The following clauses are examples and are not limiting.

Clause 1. A knit article comprising: a first location having a first knit structure including a repeating pattern of a first number of knit courses having a first yarn knit with a first basic knit stitch and a second number of knit courses having the first yarn, wherein within each knit course of the second number of knit courses, the first yarn is knit in a repeating pattern including a first number of knit stitches knit with a second basic knit stitch and a second number of float stitches.

Clause 2. The knit article according to clause 1, wherein the first number of knit stitches is the same as the second number of float stitches.

Clause 3. The knit article according to clause 1, wherein the first number of knit stitches is different from the second number of float stitches.

Clause 4. The knit article according to any of clauses 1 through 3, wherein the first number of knit courses is the same as the second number of knit courses.

Clause 5. The knit article according to any of clauses 1 through 3, wherein the first number of knit courses is different from the second number of knit courses.

Clause 6. The knit article according to any of clauses 1 through 5, wherein the first knit structure further includes a second yarn that is in a plated relationship with the first yarn.

Clause 7. The knit article according to clause 6, wherein the second yarn is continuously knit with the second basic knit stitch in the second number of knit courses.

Clause 8. The knit article according to any of clauses 6 through 7, wherein one or more of the first yarn and the second yarn is an elastic yarn.

Clause 9. The knit article according to any of clauses 1 through 8, further comprising a second location having a second knit structure, the second knit structure including a repeating pattern of a third number of knit courses having the first yarn knit with the first basic knit stitch and a fourth number of knit courses having the first yarn, wherein within each knit course of the fourth number of knit courses, the first yarn is knit in a repeating pattern including a third number of knit stitches knit with the second basic knit stitch and a fourth number of float stitches, wherein one or more of the third number of knit courses is different from the first number of knit courses, and the fourth number of float stitches is different from the second number of float stitches.

Clause 10. The knit article according to clause 9, wherein the first knit structure is integrally knit with the second knit structure.

Clause 11. A knit article comprising: a first location having a first knit structure including a repeating pattern of a first number of knit courses having a first yarn knit with a first basic knit stitch and a second number of knit courses having the first yarn, wherein within each knit course of the second number of knit courses, the first yarn is knit in a repeating pattern including a first number of knit stitches knit with a second basic knit stitch and a second number of float stitches; and a second location having a second knit structure including a repeating pattern of a third number of knit courses having the first yarn knit with the first basic knit stitch and a fourth number of knit courses having the first yarn, wherein within each knit course of the fourth number of knit courses, the first yarn is knit in a repeating pattern including a third number of knit stitches knit with the second basic knit stitch and a fourth number of float stitches, wherein one or more of the third number of knit courses is different from the first number of knit courses, and the fourth number of float stitches is different from the second number of float stitches.

Clause 12. The knit article according to clause 11, wherein one or more of the fourth number of knit courses is different from the second number of knit courses, and the third number of knit stitches is different from the first number of knit stitches.

Clause 13. The knit article according to any of clauses 11 through 12, wherein the first knit structure is integrally knit with the second knit structure.

Clause 14. The knit article according to any of clauses 11 through 13, wherein each of the first knit structure and the second knit structure further includes a second yarn that is in a plated relationship with the first yarn.

Clause 15. The knit article according to clause 14, wherein the second yarn is continuously knit with the second basic knit stitch in each of the second number of knit courses and the fourth number of knit courses.

Clause 16. The knit article according to any of clauses 14 through 15, wherein one or more of the first yarn and the second yarn includes an elastic yarn.

Clause 17. A method of knitting a knit article comprising: during a single knitting event: knitting a first knit structure at a first location of the knit article, the first knit structure including a repeating pattern of a first number of knit courses having a first yarn knit with a first basic knit stitch and a second number of knit courses having the first yarn, wherein within each knit course of the second number of knit courses, the first yarn is knit in a repeating pattern including a first number of knit stitches knit with a second basic knit stitch and a second number of float stitches; and knitting a second knit structure at a second location of the knit article, the second knit structure including a repeating pattern of a third number of knit courses having the first yarn knit with the first basic knit stitch and a fourth number of knit courses having the first yarn, wherein within each knit course of the fourth number of knit courses, the first yarn is knit in a repeating pattern including a third number of knit stitches knit with the second basic knit stitch and a fourth number of float stitches, wherein one or more of the third number of knit courses is different from the first number of knit courses, and the fourth number of float stitches is different from the second number of float stitches.

Clause 18. The method of knitting the knit article according to clause 17, wherein the float stitch in the second number of knit courses and the fourth number of knit courses extends over from two wales to five wales.

Clause 19. The method of knitting the knit article according to any of clauses 17 through 18, wherein each of the first knit structure and the second knit structure further includes a second yarn that is in a plated relationship with the first yarn.

Clause 20. The method of knitting the knit article according to clause 19, wherein the second yarn is continuously knit with the second basic knit stitch in each of the second number of knit courses and the fourth number of knit courses.

Clause 21. A knit sock comprising: a collar having a perimeter edge around an opening for receiving a wearer's foot; a leg portion extending from the collar; a foot portion extending from the leg portion and terminating at a toe end; a heel portion positioned between the leg portion and the foot portion; and an integrally knit heel band extending around a circumference of the sock and positioned at a lower end of the leg portion, the integrally knit heel band including a first portion that extends from a first location at a rear, lateral side of the heel portion, around a front side of the leg portion, and to a second location at a rear, medial side of the heel portion, the first portion including a plurality of continuously knit stitches that form a plurality of knit courses, and a second portion that extends from the first location, around a rear aspect of the heel portion, and to the second location, the second portion formed from knit courses that include a repeating pattern of a first number of knit stitches knit with a second basic knit stitch and a second number of float stitches that form float areas.

Clause 22. The knit sock according to clause 21, wherein the heel band divides the heel portion into an upper half and a lower half.

Clause 23. The knit sock according to any of clauses 21 through 22, wherein the first portion of the heel band extends around an ankle/instep area of the knit sock.

Clause 24. The knit sock according to any of clauses 21 through 23, wherein at least the second portion of the heel band is knit with a first yarn, and wherein the first yarn is an elastic yarn.

Clause 25. The knit sock according to clause 24, wherein the second portion of the heel band is knit with one or more additional yarns, and wherein at least one of the one or more additional yarns includes an elastic yarn.

Clause 26. The knit sock according to any of clauses 21 through 25, wherein the first portion of the heel band exhibits a first degree of stretch in a coursewise direction, and wherein the second portion of the heel band exhibits a second degree of stretch in the coursewise direction, the second degree of stretch less than the first degree of stretch.

Aspects of the present disclosure have been described with the intent to be illustrative rather than restrictive. Alternative aspects will become apparent to those skilled in the art that do not depart from its scope. A skilled artisan may develop alternative means of implementing the aforementioned improvements without departing from the scope of the present disclosure.

It will be understood that certain features and subcombinations are of utility and may be employed without reference to other features and subcombinations and are contemplated within the scope of the claims. Not all steps listed in the various figures need be carried out in the specific order described.

What is claimed is:

1. A knit article comprising:
  a first location having a first knit structure including a repeating pattern of a first number of knit courses having a first yarn knit with a first basic knit stitch that includes a terry loop and a second number of knit courses having the first yarn, wherein within each knit course of the second number of knit courses, the first yarn is knit in a repeating pattern including (a) a first number of knit stitches knit with a second basic knit stitch that does not include a terry loop and (b) a second number of float stitches,
  wherein the first knit structure further includes a second yarn that is in a plated relationship with the first yarn, and the second yarn is an elastic yarn.

2. The knit article of claim 1, wherein the first number of knit stitches is the same as the second number of float stitches.

3. The knit article of claim 1, wherein the first number of knit stitches is different from the second number of float stitches.

4. The knit article of claim 1, wherein the first number of knit courses is the same as the second number of knit courses.

5. The knit article of claim 1, wherein the first number of knit courses is different from the second number of knit courses.

6. The knit article of claim 1, wherein the second yarn is continuously knit with the second basic knit stitch in the second number of knit courses.

7. The knit article of claim 1, wherein the first yarn is an elastic yarn.

8. The knit article of claim 1, further comprising a second location having a second knit structure, the second knit structure including a repeating pattern of a third number of knit courses having the first yarn knit with the first basic knit stitch and a fourth number of knit courses having the first yarn, wherein within each knit course of the fourth number of knit courses, the first yarn is knit in a repeating pattern including a third number of knit stitches knit with the second basic knit stitch and a fourth number of float stitches, wherein one or more of the third number of knit courses is different from the first number of knit courses and the fourth number of float stitches is different from the second number of float stitches.

9. The knit article of claim 8, wherein the first knit structure is integrally knit with the second knit structure.

10. A knit article comprising:
a first location having a first knit structure including a repeating pattern of a first number of knit courses having a first yarn knit with a first basic knit stitch that includes a terry loop and a second number of knit courses having the first yarn, wherein within each knit course of the second number of knit courses, the first yarn is knit in a repeating pattern including a first number of knit stitches knit with a second basic knit stitch that does not include a terry loop and a second number of float stitches; and
a second location having a second knit structure including a repeating pattern of a third number of knit courses having the first yarn knit with the first basic knit stitch that includes a terry loop and a fourth number of knit courses having the first yarn, wherein within each knit course of the fourth number of knit courses, the first yarn is knit in a repeating pattern including (a) a third number of knit stitches knit with the second basic knit stitch that does not include a terry loop and (b) a fourth number of float stitches, wherein one or more of the third number of knit courses is different from the first number of knit courses and the fourth number of float stitches is different from the second number of float stitches.

11. The knit article of claim 10, wherein one or more of the fourth number of knit courses is different from the second number of knit courses, and the third number of knit stitches is different from the first number of knit stitches.

12. The knit article of claim 10, wherein the first knit structure is integrally knit with the second knit structure.

13. The knit article of claim 10, wherein each of the first knit structure and the second knit structure further includes a second yarn that is in a plated relationship with the first yarn.

14. The knit article of claim 13, wherein the second yarn is continuously knit in the second basic knit stitch in each of the second number of knit courses and the fourth number of knit courses.

15. The knit article of claim 13, wherein one or more of the first yarn and the second yarn includes an elastic yarn.

16. A method of knitting a knit article comprising:
during a single knitting event:
knitting a first knit structure at a first location of the knit article, the first knit structure including a repeating pattern of a first number of knit courses having a first yarn knit with a first basic knit stitch that includes a terry loop and a second number of knit courses having the first yarn, wherein within each knit course of the second number of knit courses, the first yarn is knit in a repeating pattern including (a) a first number of knit stitches knit with a second basic knit stitch that does not include a terry loop and (b) a second number of float stitches; and
knitting a second knit structure at a second location of the knit article, the second knit structure including a repeating pattern of a third number of knit courses having the first yarn knit with the first basic knit stitch that includes a terry loop and a fourth number of knit courses having the first yarn, wherein within each knit course of the fourth number of knit courses, the first yarn is knit in a repeating pattern including (a) a third number of knit stitches knit with the second basic knit stitch that does not include a terry loop and (b) a fourth number of float stitches, wherein one or more of the third number of knit courses is different from the first number of knit courses and the fourth number of float stitches is different from the second number of float stitches.

17. The method of knitting the knit article of claim 16, wherein the float stitch in the second number of knit courses and the fourth number of knit courses extends over from two wales to five wales.

18. The method of knitting the knit article of claim 16, wherein each of the first knit structure and the second knit structure further includes a second yarn that is in a plated relationship with the first yarn.

19. The method of knitting the knit article of claim 18, wherein the second yarn is continuously knit in the second basic knit stitch in each of the second number of knit courses and the fourth number of knit courses.

20. The knit article of claim 1, wherein the knit article comprises at least a portion of a sock, an upper-body garment, a lower-body garment, an extremity sleeve, an upper for a shoe, a glove, or a hat.

* * * * *

UNITED STATES PATENT AND TRADEMARK OFFICE
CERTIFICATE OF CORRECTION

PATENT NO. : 11,849,773 B2
APPLICATION NO. : 17/525623
DATED : December 26, 2023
INVENTOR(S) : Amir H. Morgan et al.

Page 1 of 1

It is certified that error appears in the above-identified patent and that said Letters Patent is hereby corrected as shown below:

On the Title Page

Column 1, Item (72), Line 7, Inventor information, in the line reading "Mohamed Omar, Der Al Asad (IL);" should read --Mohamed Omar, Deir Al Asad (IL);--.

Page 3, Column 1, Line 2, Other Publications, in the line reading "nike.com, Available on Internet at: <https://web.archive.or g/web/" should read --nike.com, Available on Internet at: <https://web.archive.org/web/--.

Page 3, Column 1, Line 3, Other Publications, in the line reading "20170930140827 /hllps://news.nike.corn/news/nba-socks>, Sep. 15," should read --20170930140827 /https://news.nike.corn/news/nba-socks>, Sep. 15,--.

Page 3, Column 1, Line 16, Other Publications, in the line reading "Socks, for Yoga Pilales & Barre (Fits Women's Shoe Size 8-14)," should read --Socks, for Yoga Pilates & Barre (Fits Women's Shoe Size 8-14),--.

Page 3, Column 1, Line 18, Other Publications, in the line reading "at: <htlps://www.amazon.com/dp/B071W2JX XR>, Oct. 26, 2017," should read --at : <https://www.amazon.com/dp/B071W2JX XR>, Oct. 26, 2017,--.

Signed and Sealed this
Eighteenth Day of June, 2024

Katherine Kelly Vidal
*Director of the United States Patent and Trademark Office*